(12) United States Patent
Kovacs

(10) Patent No.: US 12,396,910 B2
(45) Date of Patent: Aug. 26, 2025

(54) EQUALIZER CLAMP ASSEMBLY, SYSTEM AND METHOD

(71) Applicant: INNOVATIVE MEDICAL PRODUCTS, INC., Plainville, CT (US)

(72) Inventor: Tamas Kovacs, Burlington, CT (US)

(73) Assignee: INNOVATIVE MEDICAL PRODUCTS, INC., Plainville, CT (US)

( * ) Notice: Subject to any disclaimer, the term of this patent is extended or adjusted under 35 U.S.C. 154(b) by 0 days.

(21) Appl. No.: 18/338,691

(22) Filed: Jun. 21, 2023

(65) Prior Publication Data

US 2023/0338218 A1 Oct. 26, 2023

Related U.S. Application Data

(63) Continuation-in-part of application No. 17/857,535, filed on Jul. 5, 2022, now Pat. No. 11,717,459, and a continuation of application No. 17/073,334, filed on Oct. 17, 2020, now Pat. No. 11,400,006.

(60) Provisional application No. 62/916,674, filed on Oct. 17, 2019.

(51) Int. Cl.
*A61G 13/10* (2006.01)
*A61B 90/57* (2016.01)
*F16B 2/12* (2006.01)

(52) U.S. Cl.
CPC ............ *A61G 13/101* (2013.01); *A61B 90/57* (2016.02); *F16B 2/12* (2013.01)

(58) Field of Classification Search
CPC .......... A61G 13/101; A61B 90/57; F16B 2/12
See application file for complete search history.

(56) References Cited

U.S. PATENT DOCUMENTS

| 6,499,158 | B1 * | 12/2002 | Easterling | A61G 15/10 |
| | | | | 5/601 |
| 7,520,007 | B2 | 4/2009 | Skripps | |
| 7,686,267 | B2 | 3/2010 | Dasilva | |
| 8,083,198 | B2 | 12/2011 | Stabler | |
| 8,485,509 | B2 * | 7/2013 | Wang | B24B 41/06 |
| | | | | 269/95 |

(Continued)

*Primary Examiner* — Anita M King
(74) *Attorney, Agent, or Firm* — Wasserbauer Law, LLC; Damian G. Wasserbauer, Esq.; Nicholas E. Blanton, Esq.

(57) ABSTRACT

A multi-directional, equalizer clamp device is disclosed, the clamp device being configured to attach and secure objects, such as posts, rails and the like, for a multiplicity of clamping applications that benefit from single-point clamping operation. The clamp device comprises upper and lower body portions which may be configured to clamp to a side rail of a support table, while further configured to receive objects and clamp them along a secondary clamping direction. The clamp device further comprises a control assembly, such as a knob, to facilitate and achieve simultaneous clamping along both primary and secondary clamping directions at a single point of control. A jogging clamp for clamping to variable sized objects in a primary direction comprises a plurality of spherical, indexing recesses disposed in the lower jaw and matching spherical washer disposed on the control assembly configured to allow large, indexed vertical variation in the clamping range.

7 Claims, 14 Drawing Sheets

(56) References Cited

U.S. PATENT DOCUMENTS

| | | | | |
|---|---|---|---|---|
| 9,022,334 | B1* | 5/2015 | DeMayo | A61G 13/101 |
| | | | | 248/229.24 |
| 9,585,806 | B2 | 3/2017 | Herrig | |
| 11,548,118 | B2* | 1/2023 | Ghinassi | B25B 5/087 |
| 11,957,628 | B2* | 4/2024 | Kovacs | A61F 5/3776 |
| 2014/0007408 | A1* | 1/2014 | Nool | B65D 25/22 |
| | | | | 29/525.01 |

\* cited by examiner

EQUALIZER CLAMP ASSEMBLY, SYSTEM AND METHOD

CROSS REFERENCE TO RELATED APPLICATIONS

This application is a continuation-in-part of, claims priority to, and the benefit of, co-pending U.S. Non-Provisional application Ser. No. 17/857,535, filed Jul. 5, 2022, entitled, "SINGLE-ACTION, MULTI-DIRECTIONAL CLAMP ASSEMBLY, SYSTEM AND METHOD", which claims priority to Ser. No. 17/073,334, filed Oct. 17, 2020, granted U.S. Pat. No. 11,400,006 issued on Aug. 2, 2022, entitled, "EQUALIZER CLAMP ASSEMBLY, SYSTEM AND METHOD", which in turn claims priority to 62/916,674, filed Oct. 17, 2019, entitled, "EQUALIZER CLAMP ASSEMBLY, SYSTEM AND METHOD", of which the disclosures are incorporated by reference herein in their entirety.

FIELD OF THE INVENTION

The present invention relates to a clamp assembly and, more particularly, to a clamp apparatus, system and method for simultaneously locking multiple components with different orientations.

BACKGROUND OF THE INVENTION

When clamping multiple components with different orientations, conventional clamps use individual forcing mechanisms in order to secure each object to the clamp body. For example, a clamp may have a primary opening to secure to an object (e.g., a rail, rod, bar, standing seam, or the like) in one direction (e.g., x-direction) and other openings to insert other objects disposed in another direction (e.g., y-direction). For the opening(s) in each separate direction, e.g., x or y, a separate mechanism is used to apply force to the clamp body such as, for example, a knob, handle, or other tightening device to urge the parts of the clamp body to tighten and/or loosen around the object. The additional components for each forcing mechanism add complexity and cost to the manufacturing of the clamp assembly. It would be advantageous to reduce the number of components in the clamp assembly as well as to use a single forcing mechanism to operate the clamp for multiple objects, e.g., using a single knob or handle.

Consequently, there is a need for a clamp apparatus, system and method using a fastener and/or forcing mechanism having a single action for locking multiple objects disposed in different numerous directions that achieves clamping in multiple directions simultaneously.

SUMMARY OF THE INVENTION

The present invention provides numerous applications in various industries would benefit from such a clamp assembly. For example, a clamp assembly application to attach objects to the side rail of a surgical support can improve access to the patient for the surgeon. It is to be appreciated by one of skill that the clamping can be arranged on the side rail of a support table in either direction. The invention is described using an upper portion and a lower portion for the body parts of the clamp, which is merely for convenience of illustration and should not be deemed limiting to the invention in any way.

A clamp assembly for surgical procedures further requires sterilization and improved sterilization can be accomplished with a clamp body having open channels that may be cleared by standard sterilization techniques.

Applications also exist in attaching a clamp assembly to various objects and/or structures. For example, a single action fastener that clamps multiple objects can be used advantageously in connection with a clamp assembly for the standing seam of the metal roof, thereby reducing the time of the installer on the roof and/or structure, use of available space, costs of manufacturing, and improving the aesthetic appearance of these objects installed on the structure. As will be appreciated by one skilled in the art, the clamp apparatus, system and method may find further used for other applications to clamp other items and things including mounting to a structure such as a wall, shingled roof or other rooftop, and other structures.

DETAILED DESCRIPTION OF INVENTION(S)

Figure 1:
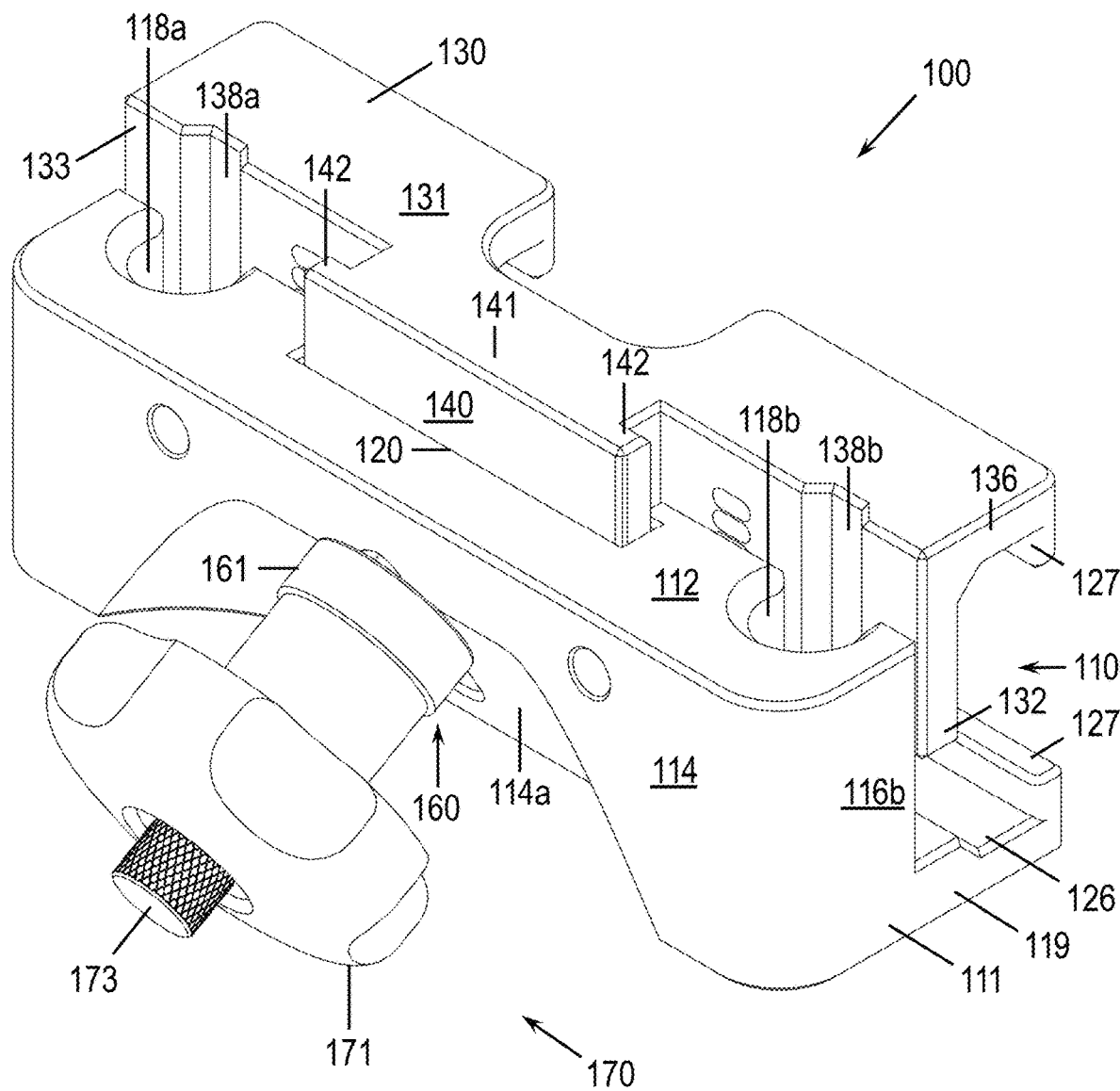
FIG. 1 illustrates a front, top, right, perspective view of a clamp apparatus for clamping multiple objects disposed in different orientations using a single fastener and/or forcing mechanism, according to a first embodiment of the invention.

Non-limiting embodiments of the present invention will be described below with reference to the accompanying drawings, wherein like reference numerals represent like elements throughout. While the invention has been described in detail with respect to the preferred embodiments thereof, it will be appreciated that upon reading and understanding of the foregoing, certain variations to the preferred embodiments will become apparent, which variations are nonetheless within the spirit and scope of the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are provided for the purposes of illustrating some embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

FIGS. 1 through 7A-7E illustrate certain embodiments and features generally shown as clamp apparatus, system, and method 100. One or more of the concepts described therein may be useful in combination with the teachings of U.S. Non-Provisional application Ser. No. 17/857,535 and variations and combinations thereof. Consequently, clamp 100 is described generally in the environment of surgical positioners that is non-limiting as clamp 100 may be useful for a variety of applications such as in the construction industry, and other fields of use. Another intended use for clamp 100 may be to secure and hold a work tablet or electronic device, for ease of use and display while in the field. Further examples of intended use may be clamping, either alone or in combination with a device or object, of or to a solar panel, a snow rail system, HVAC equipment, electrical equipment, structural equipment, and/or construction equipment. Therefore, the applications of clamp 100 are also non-limiting.

Figure 2:
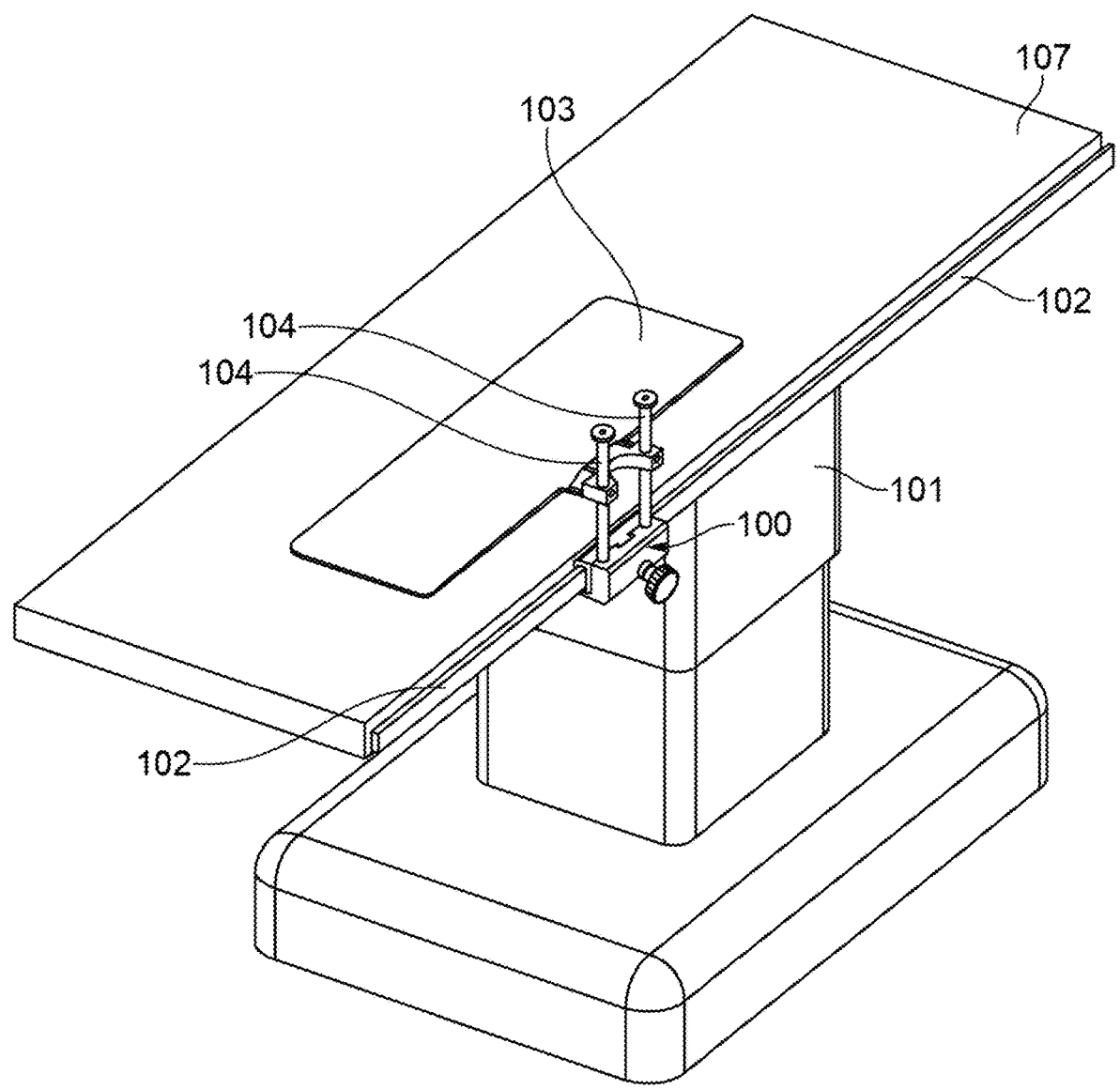
FIG. 2 illustrates a perspective view of the clamp apparatus of FIG. 1 in the environment of attaching a surgical positioner using elongated posts and/or pins to a side rail of a support table, according to an embodiment of the invention.
Figure 3A:
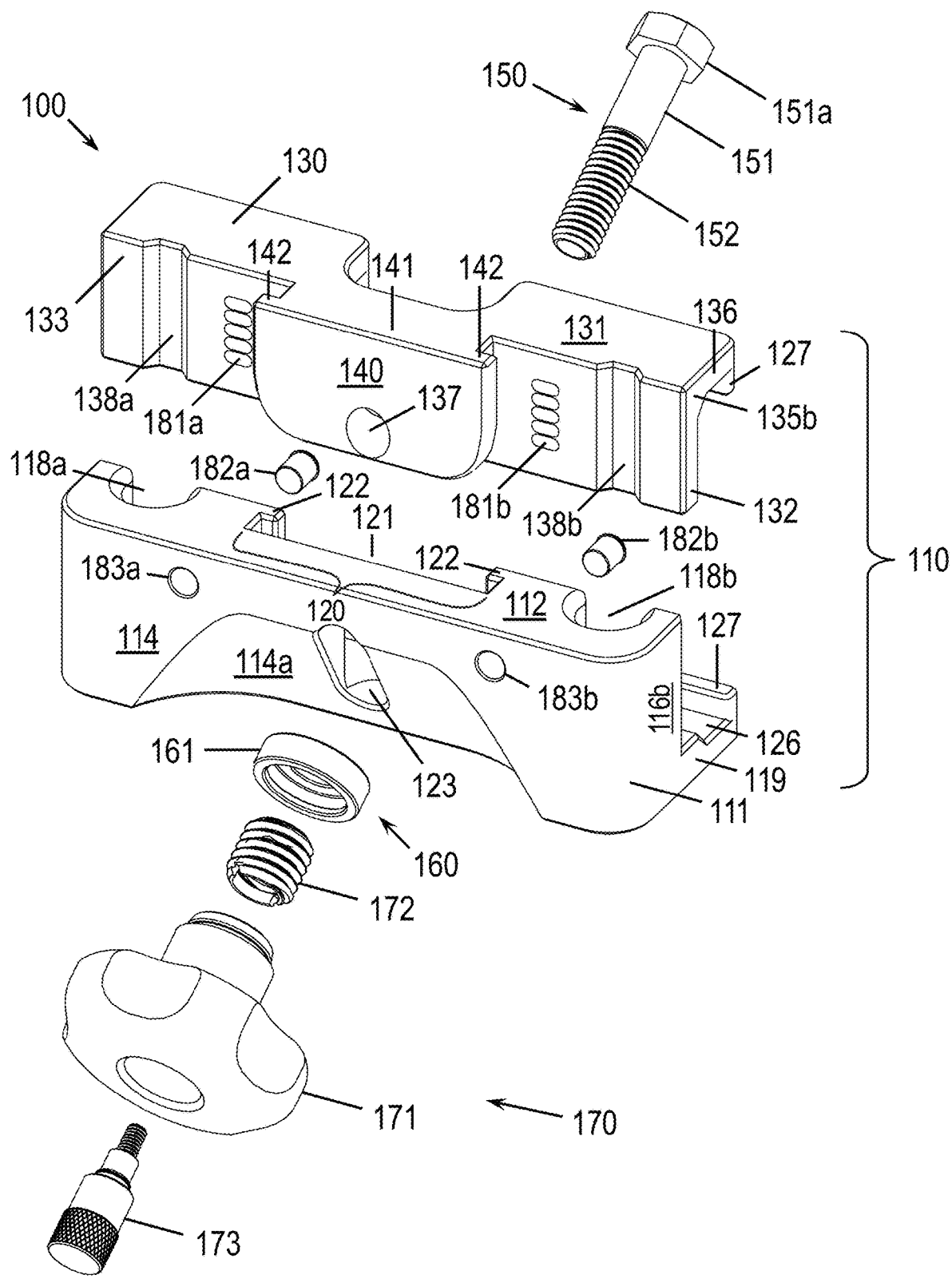
FIG. 3A illustrates an exploded, front, top, right, perspective view of a clamp apparatus for clamping multiple objects disposed in different orientation using a single fastener and/or forcing mechanism thereof.
Figure 3B:
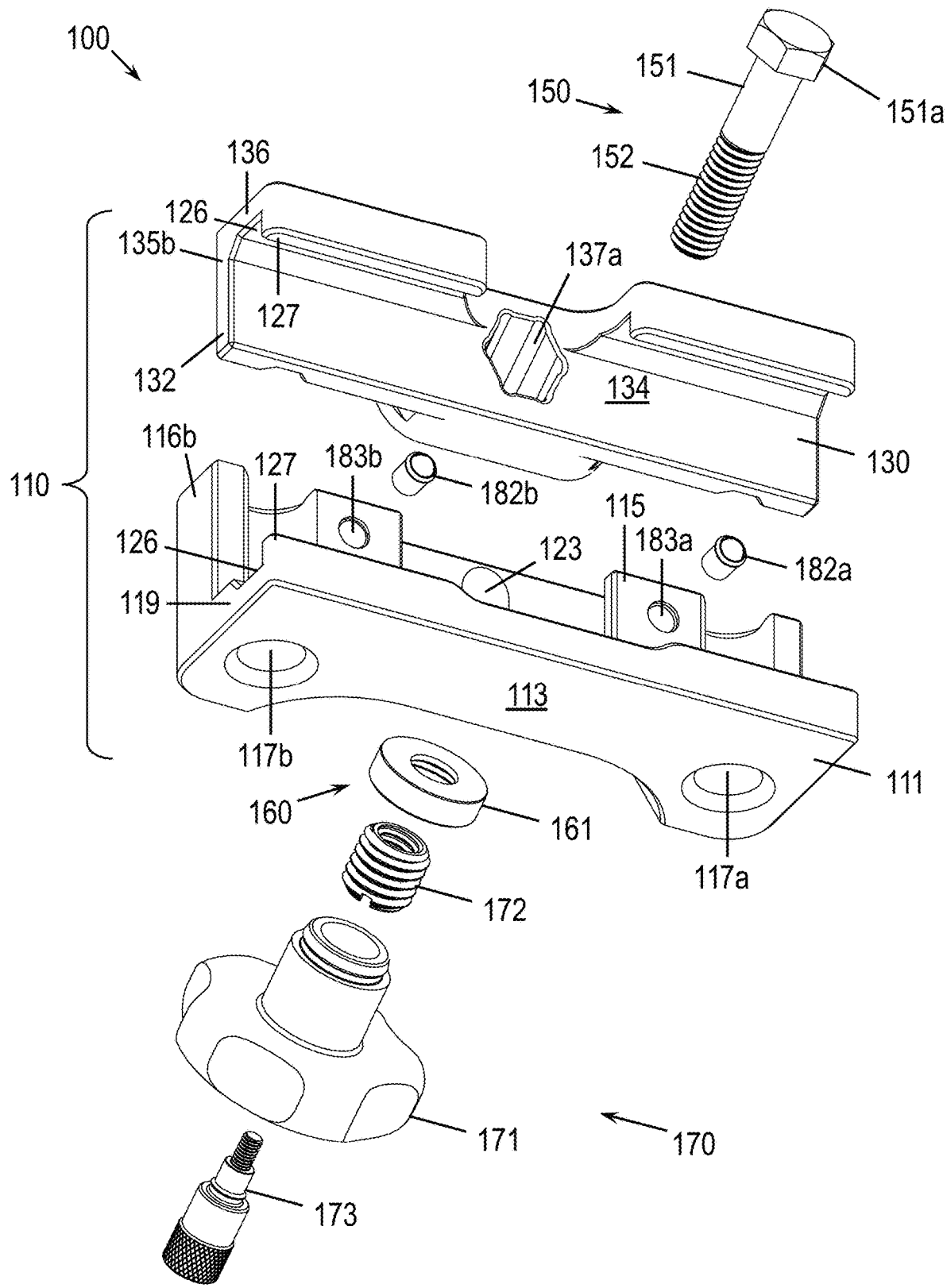
FIG. 3B illustrates an exploded, rear, bottom, right, perspective view of a clamp apparatus for clamping multiple objects disposed in different orientation using a single fastener and/or forcing mechanism thereof.
Figure 4A:
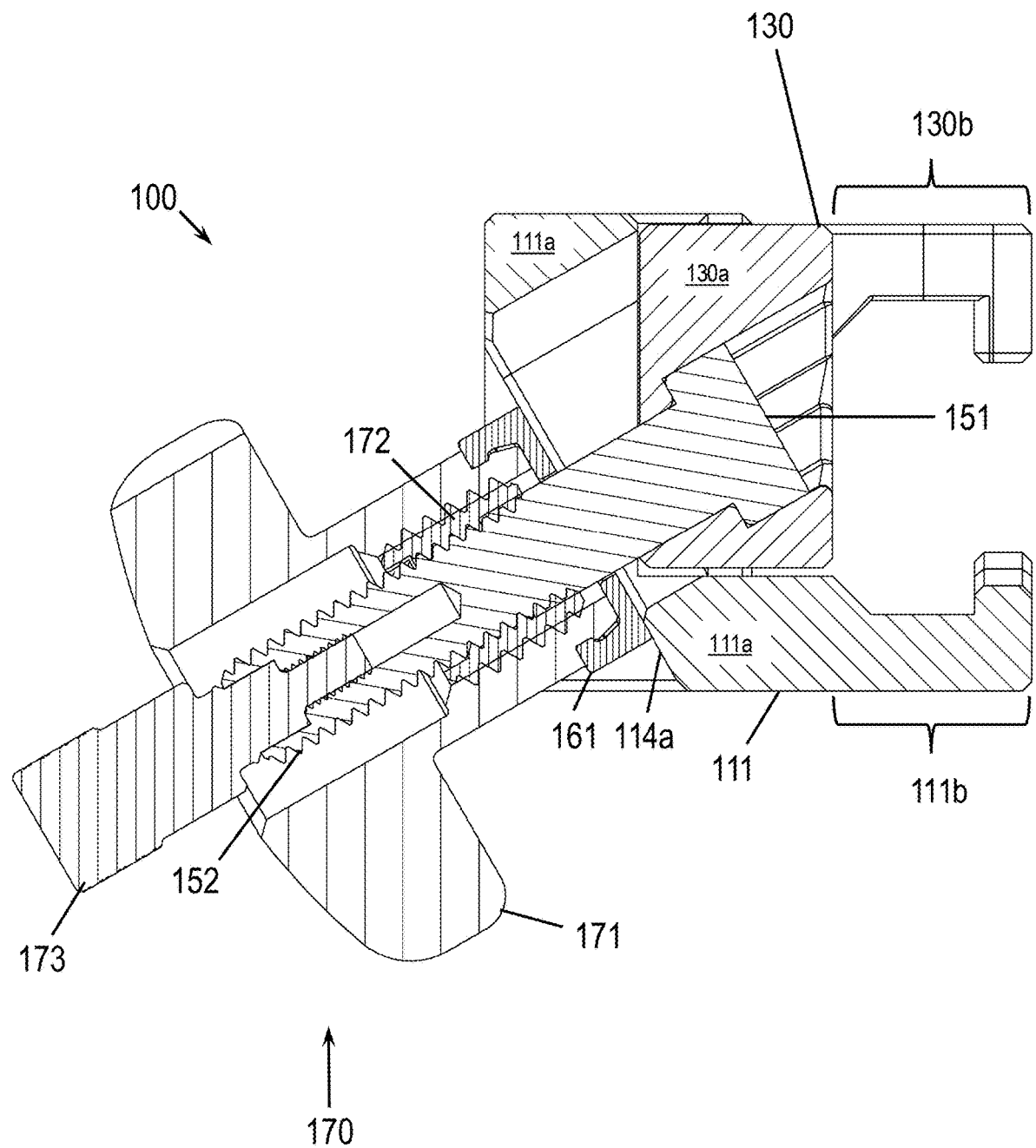
FIG. 4A illustrates a section view of the clamp apparatus of FIG. 1 in a closed position thereof.

Referring to FIGS. 1 to 4A-4B illustrating a first embodiment for a clamp apparatus, system, and method for a single-action clamp capable of locking multiple components disposed in a variety of orientations is generally shown as element 100. The clamp 100 may comprise four component parts: a clamp assembly 110, a fastener assembly 150, a washer assembly 160, and a control assembly 170. The clamp assembly 110 may comprise an upper body 111 configured to operatively connect to a lower body 130. The fastener assembly 150 may comprise a hex bolt 151 with a threaded portion 152 configured to be disposed through fastener openings 123, 137 of the upper body 111 and lower body 130, respectively, so as to join using forces applied by a washer assembly 160 and control assembly 170. The upper body 111 of the clamp assembly 110 comprises the top portion 112, a bottom portion 113, a front portion 114, a back portion 115 portion, and side portion 116 that is designated as individual sides 116a and 116b. The upper body 111 may also be considered as including an upper base 111a and an upper arm 111b, as shown in FIG. 4A. The upper body 111 may further comprise one or more openings 117, designated as openings 117a and 117b, shown in FIG. 3B, and which can be formed between the top portion 112 and the bottom portion 113, and extend therethrough. As illustrated in FIG. 2, the openings 117a and 117b of FIG. 3B may be configured to receive one or more posts 104 for attaching, for example, a patient positioner 103 to the side rail 102 of the operating room table 101 according to an embodiment of the invention. The upper body 111 also comprises one or more slot openings 118 designated as slot openings 118a and 118b in FIGS. 1 and 3A. The slot openings 118a and 118b are configured to receive one or more posts 104 for attaching a patient positioner 103 to the side rail 102 of the support table 107, as shown in FIG. 2, according to an embodiment of the invention. The clamp assembly 110 can be assembled such that the slot openings 118a and 118b are located adjacent the slot recesses 138 designated as slot recesses 138a and 138b in FIGS. 1 and 3A, to accomplish single action locking of multiple components in different orientations. The upper body 111 comprises a back portion 115 that can be configured with a upper side rail arm 119 that can further have a side rail register 126 and a side rail lip 127 so as to couple the clamp 100 to the side rail 102. The upper body 111 also comprises a channel portion 120 having a slot segment 121 and shoulder segment 122 adapted to be operably connected to and receive a key protrusion 140 and corresponding slot segment 141 and shoulder segment 142 that may be formed in the lower body 130 of the clamp assembly 110.

The upper body 111 comprises one or more fastener openings 123 disposed in an angled portion 114a of the front portion 114 and extending through to the back portion 115, so as to receive the fastener assembly 150 therein. Similarly, the lower body 130 comprises one or more fastener head openings 137, such that operably connecting the channel portion 120 and the key protrusion 140 disposes the one or more fastener openings 123 and the one or more fastener head openings 137 in aligned relationship, such that the fastener assembly 150 may extend through the fastener opening 123. The fastener head opening may have one or more rotational inhibitors 137a that interfere with a rotational motion of the hex bolt 151. Furthermore, the washer assembly 160 may then be disposed on the threaded portion 152 of the hex bolt 151 of the fastener assembly 150 extending therethrough, such that the control assembly 170 may be secured thereto, as shown in FIGS. 1-4B. The fastener opening 123 may be in the form of a slot allowing for vertical translation of the washer 160 and control 170 assemblies during tightening of the control knob 171. Although the bolt 151 is represented herein as having a hexagonal head 151a, the shape of the bolt head 151a may take any shape other than hexagonal, including but not limited to a head having at least one protrusion that is sufficient to maintain a constant rotational position of the bolt head 151a with respect to, e.g., the lower body 130. For example, the bolt head 151a may be square shaped or triangular shaped such that as control assembly 170 is tightened or loosened, the bolt head 151a remains in the same rotational position.

In operation, tightening control assembly 170 forces the upper body 111 and the lower body 130 toward one another to achieve clamping forces in multiple directions simultaneously. In a first securing operation, a clamping force may be achieved in a direction that allows upper and lower bodies 111 and 130 to fixedly attach to, for example, a rail 102. In a second securing operation, a clamping force may be achieved in a direction that allows upper and lower bodies 111 and 130 to fixedly attach to, for example, a post 104. The shapes are non-limiting thereto that are secured by the upper and lower portions as contemplated herein as items or components may take any shape, e.g., circular, square, rectangular. Consequently, equivalent structures may be used to connect to other items or components so that these may be affixed via clamp 100 and are allowed to move in multiple directions regarding the first and second directions.

The lower body 130 comprises a top portion 131, a bottom portion 132, a front portion 133, a back portion 134, and side portion 135 that is designated as individual sides 135a and 135b. The lower body 130 may also be considered as including a lower base 130a and a lower arm 130b, as shown in FIG. 4A. The top portion 131 and front portion 133 comprise a key protrusion 140 extending therefrom. The key protrusion 140 comprises a slot segment 141 and a shoulder segment 142. The lower body 130 of the clamp body assembly has a lower side rail arm 136 extending from the top portion 131 that may have a similar side rail register 126 and side rail lip 127 for ease of registering on the side rail 102 of a support table 101. The support table 101 may be configured with a tabletop or upper table surface 107. In one embodiment, the lower body 130 further comprises one or more slot recess 138, designated as individual slot recess 138a and 138b, so as to form points of connection, along with slot openings 118a and 118b, configured to receive posts 104. The lower body 130 further includes one or more fastener head openings 137 receiving the hex bolt 151 of the fastener assembly 150 that can be located and formed by a milled slot extending partially in the lower body 130 between the front portion 133 and the back portion 134. In this manner, the clamp assembly 110 can be assembled such that the slot openings 118a and 118b can be located adjacent respective slot recesses, 138a and 138b, to accomplish single action locking. By tightening the control assembly 170, which advances washer assembly 160 along threaded portion 152 of the fastener assembly 150 toward hex bolt 151, the clamp 100 achieves a clamping force where, for example, the upper body 111 and lower body 130 are forced in two directions simultaneously.

Figure 4B:
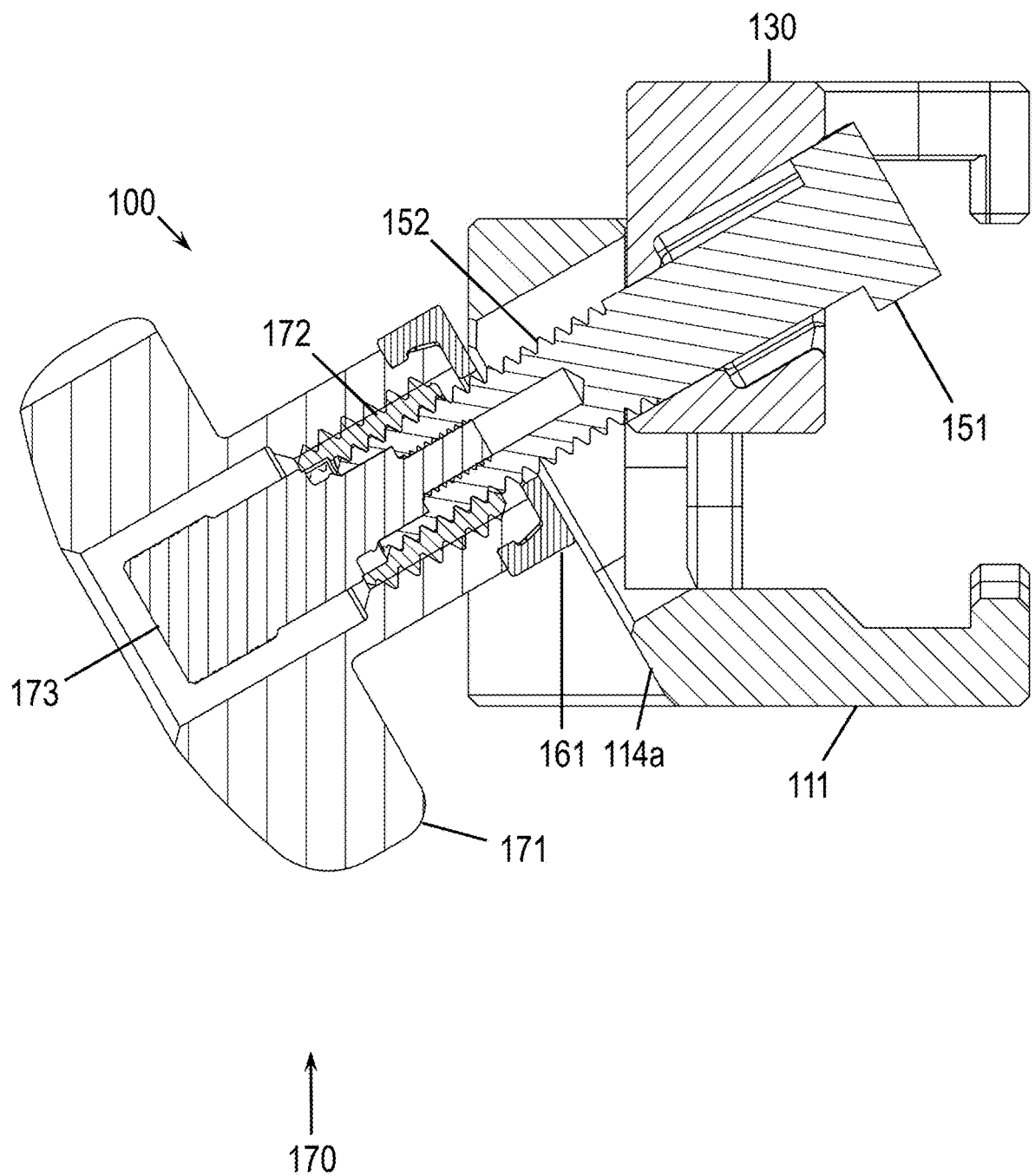
FIG. 4B illustrates a section view of the clamp apparatus of FIG. 1 in an open position thereof.

FIGS. 4A-4B illustrate the alignment of the fastener 150, washer 160 and control assemblies 170 when the clamp assembly 100 is in a clamped or loosely clamped position. FIG. 4A shows the assembled arrangement of the components of the control assembly 170, including a knob 171 which is fitted with a threaded insert 172 whose threads mate with the fastener threads 152. The threaded end 152 of the fastener 151 is further coupled to a threaded stop 173, which is assembled to the fastener 151 through an opening in the knob 171. Referring to FIG. 4B, the threaded stop 173 is of a diameter larger than the inner diameter of the threaded insert 172 such that upon loosening of the fastener 151 while still engaged with the threaded insert 172, the fastener 150, washer 160 and control assemblies are not completely disassembled. Since the threads of the fastener 152 and threaded insert 172 remain engaged, simple tightening of the knob 171 results in closing of the clamp assembly 110. This loosely coupled arrangement of the clamp 100 further facilitates single handed operation.

The lower 130 and upper 111 bodies may comprise indexing features 180 that facilitate one-handed operation of the clamp. When in operation the clamp 100 must be repositioned, or alternatively, when posts 104 must be inserted, removed or repositioned, it is desirable that, upon loosening of the fastener assembly 170, only a small amount of vertical movement is allowed while the lower 130 and upper 111 bodies remain engaged. Referring to FIG. 3, this is achieved on the lower body 130 by two sets of indexing recesses 181a, 181b disposed in the lower front portion 133 and on the upper body 111 by spring loaded pins 182a, 182b disposed in holes 183a, 183b in the back portion 115 thereof. In operation, when the lower 130 and upper 111 bodies are in close proximity, pins 182a, 182b each engage one of a plurality of indexing recesses 181a, 181b thereby retaining the vertical alignment of the bodies 130, 111. For example, a vertical opening movement between the bodies 130, 111 is possible by single hand squeezing of the top portion 131 of the lower body 130, and the bottom 113 of the upper body 111. Conversely, a vertical closing movement between the bodies 130, 111 is possible by single hand squeezing of the top 112 of the upper body 111, and the bottom 132 of the lower body 130. Because of the indexing retention of the upper and lower bodies 130, 111, the hand may release the clamp assembly and move to the control assembly without the clamp falling off the rail 102. This frees a second hand for another simultaneous task, an important advantage in, for example, a structure, support table. and/or in an operating room environment.

Relative dimensions of the components that comprise clamp 100 may vary depending on the purpose served, for example, clamping the side rail 102 and clamping to the posts or pins 104. However, clamp assembly 110, fastener assembly 150, washer assembly 160, and control assembly 170 may be dimensioned differently for another application, such as clamping objects to the standing seam of a metal roof. In the first example, primary clamping is to be performed to operably connect the clamp body assembly 110 to the side rail 102 by the side rail arms 119 and 136 being pulled together by the tightening of the control assembly 170 advancing on the threaded portion 152 of fastener 151 and pressing the washer assembly 160 against the upper body 111. Once the side rail 102 is compressed by the side rail arms 119, 136, e.g., in the vertical plane, advancing the knob 171 on the threads 152 moves the fastener assembly 150 in the openings of the channel portion 120 and key portion 140, whereby the slotted fastener opening 123 of the upper body 111 causes the fastener 150 and control 170 assemblies to compress the back portion 115 of the upper body 111 towards the front portion 133 of the lower body 130 of the clamp assembly 110. This action secures the posts 104 in the openings 117 (117a, 117b), and the portions of posts 104 that protrude radially from the slot openings 118 (118a, 118b) are engaged by the slot recesses 138 (138a, 138b), thereby achieving a compressing effect in the horizontal plane. The directions in which clamping is effected may be mutually orthogonal, wherein compressive forces act in the horizontal and vertical direction, or alternatively compressing forces may act in non-orthogonal, but offset, directions, depending on the application.

Figure 5:
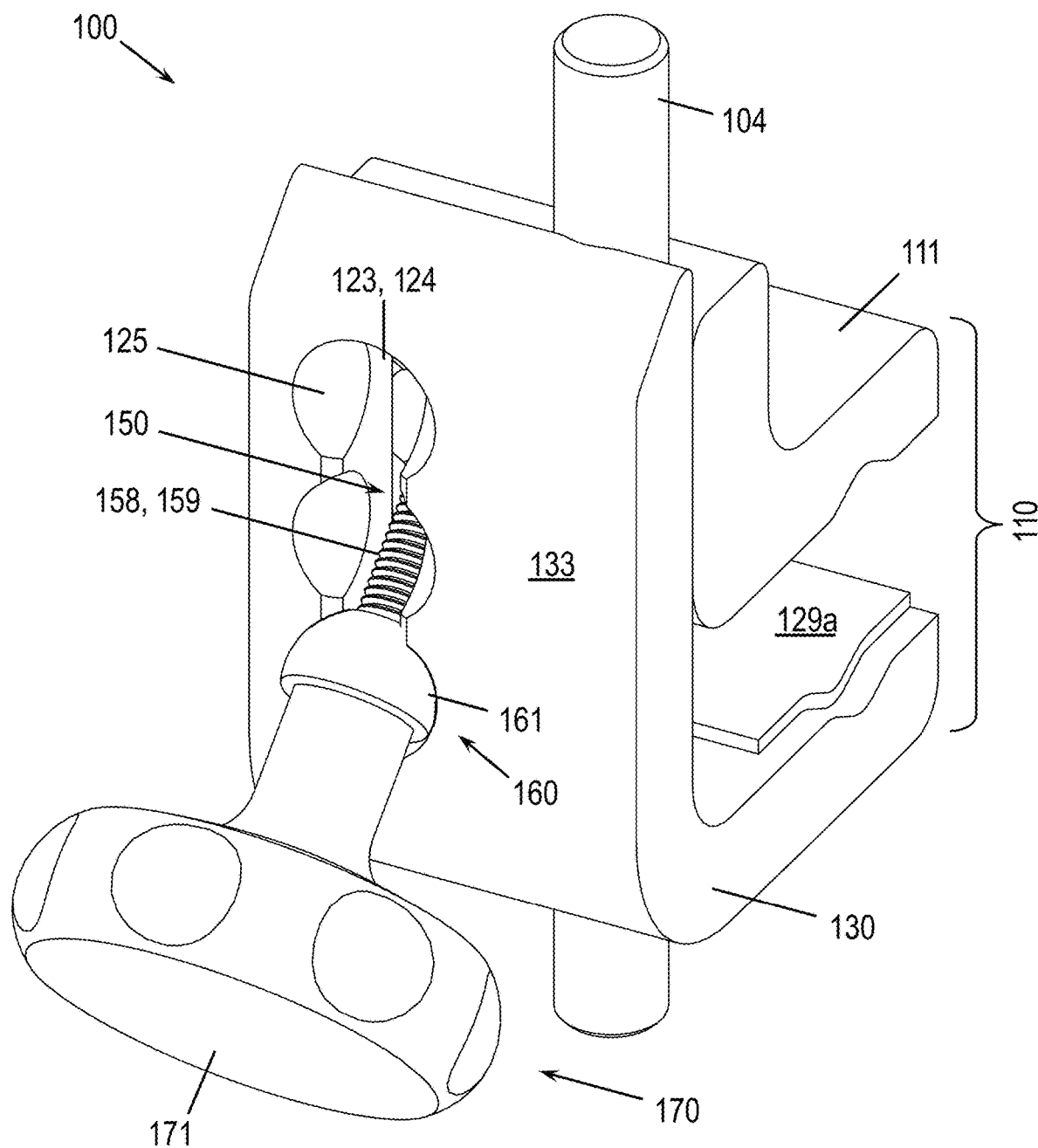
FIG. 5 illustrates a front, top, right, perspective view of a clamp apparatus for clamping multiple objects disposed in different orientation using a single fastener and/or forcing mechanism, according to another embodiment of the invention.
Figure 6A:
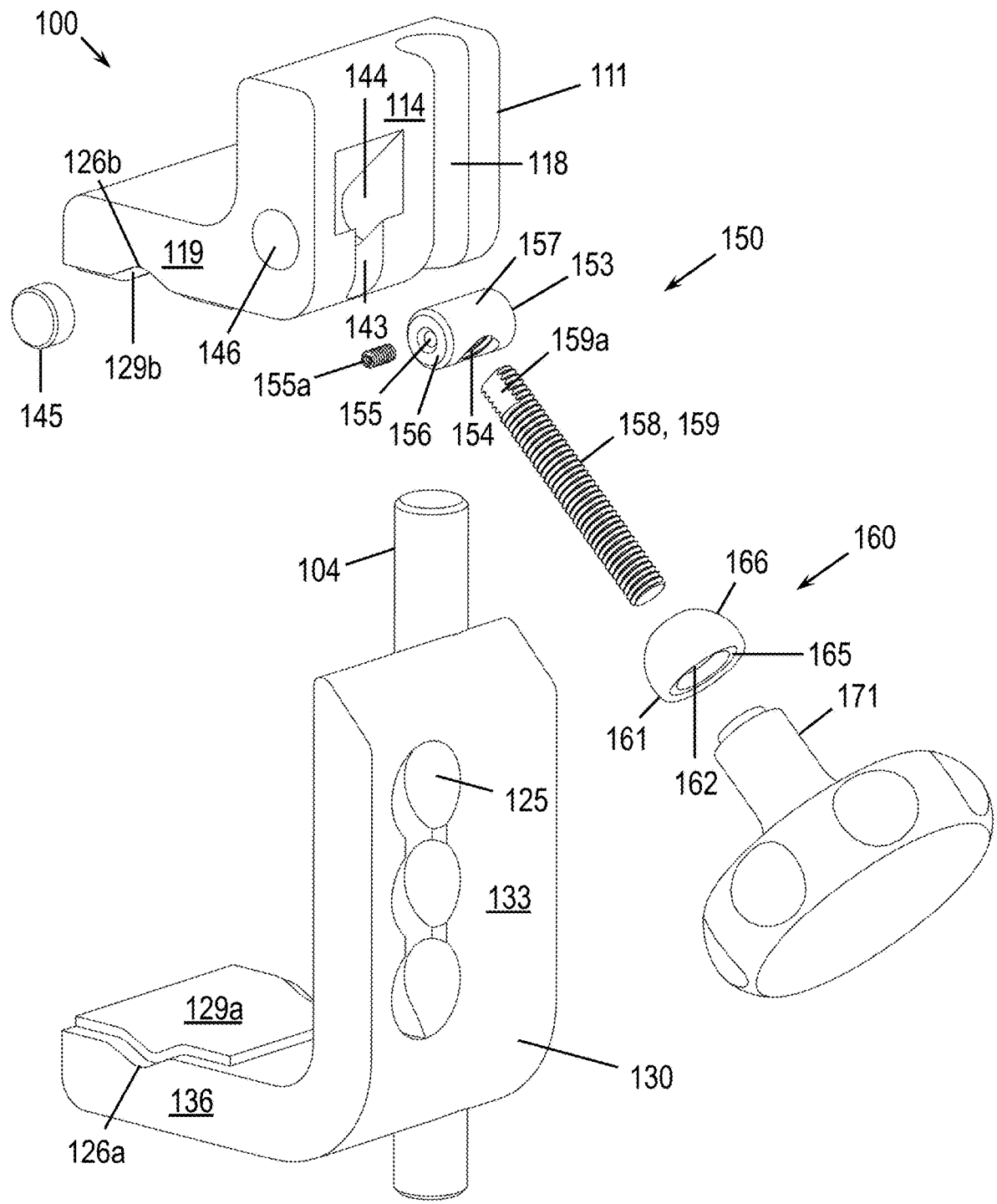
FIG. 6A illustrates an exploded, front, top, left, perspective view of a clamp apparatus for clamping multiple objects disposed in different orientation using a single fastener and/or forcing mechanism thereof.
Figure 6B:
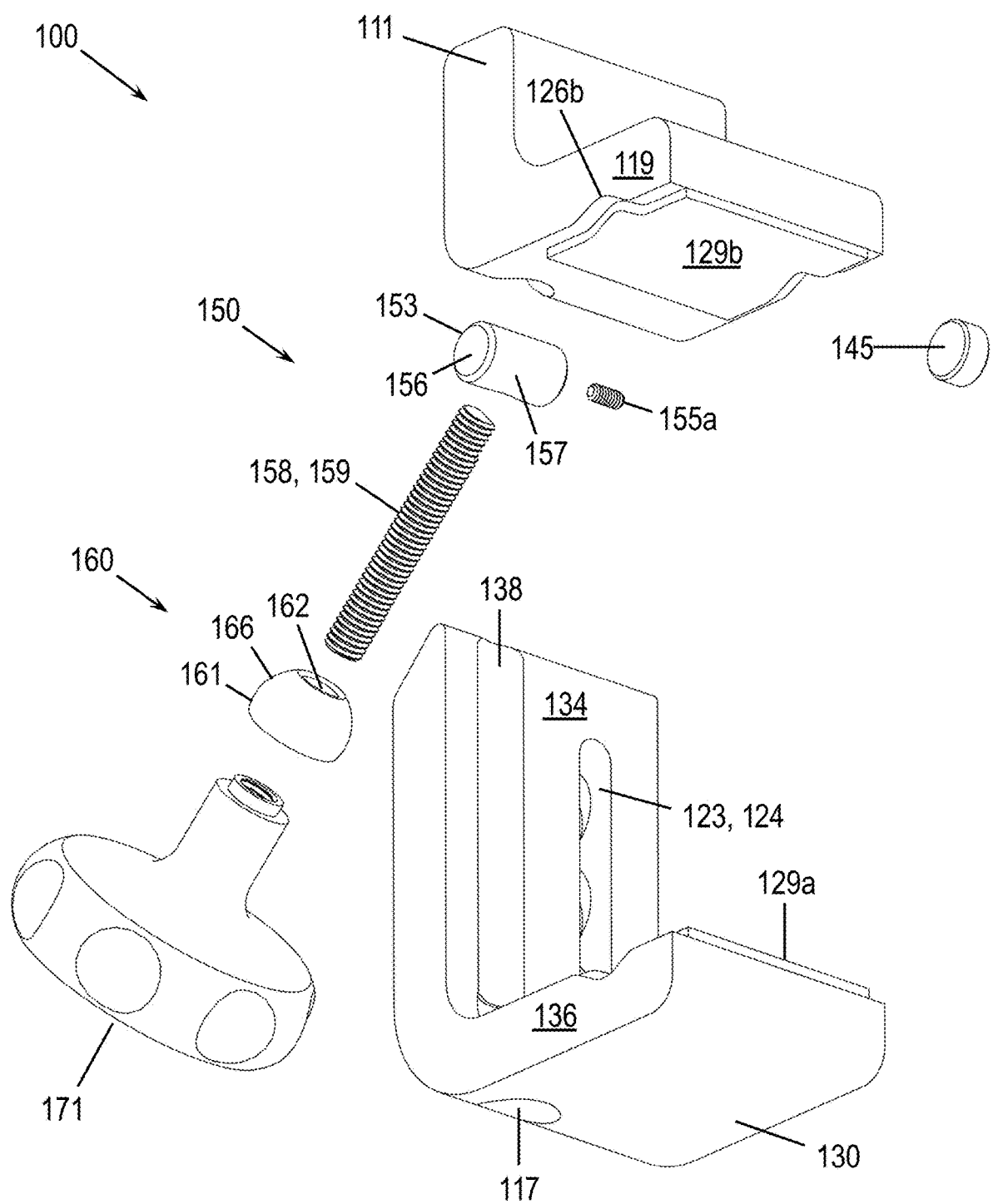
FIG. 6B illustrates an exploded, rear, bottom, right, perspective view of a clamp apparatus for clamping multiple objects disposed in different orientation using a single fastener and/or forcing mechanism thereof.

Referring to FIGS. 5-7E, a second embodiment for a clamp apparatus, system and method for a single action locking multiple components in different orientations is generally shown as element 100. The clamp 100 has four component parts: a clamp assembly 110, a fastener assembly 150, a washer assembly 160, and a control assembly 170. The clamp assembly 110 comprises an upper body 111 configured to operatively connect to a lower body 130. The upper body 111 comprises an upper front portion 114 and an upper side rail arm 119 with an upper side rail register 126b for engaging a rail, tube or other elongated object. The lower body 130 comprises a lower front portion 133, a lower back portion 134, and a lower side rail arm 136 with a lower side rail register 126a for engaging a rail, tube or other elongated object. Referring to FIG. 6B, the lower body 130 comprises an opening 117 for a post 104, rod, tube or other cylindrical object to be fixedly attached by the clamp apparatus 100. The lower body 130 also comprises a slot recess 138 configured to receive a post 104. The clamp assembly 110 can be assembled such that the slot recess 138 is located adjacent the slot opening 118 in the upper body 111, best viewed in FIG. 6A, to accomplish single action locking of multiple components in different orientations. The slot recess 138 in the lower body 130 engages the portion of the post 104 that radially protrudes from the slot opening 118 in the upper body 111. Optional pads 129a, 129b may be used to protect the surface finish of the rail or tube (not shown) and provide additional friction for clamp stability. The fastener assembly 150 comprises a T-segment 153 with cylindrical surface 157 and flat ends 156. A threaded hole 154 is disposed in the cylindrical surface 157 approximately at its midpoint and is configured to receive a stem 158 with a threaded portion 159 orthogonally oriented to the T-segment 153. A flat 159a is disposed in the threaded portion 159 of the stem 158 at the end that is inserted into the threaded hole 154. An axial, threaded hole 155 is disposed in the T-segment and opens into the threaded hole 154 disposed in the cylindrical surface 157. The axial, threaded hole 155 is configured to receive a set screw 155a that engages the flat 159a in the threaded stem 158 and retains it in the fastener assembly 150. Alternatively, the T-swivel configuration of the fastener assembly 150 may comprise a pin through a hole in the stem 158, the pin inserted through an opening 146 in the upper body 111 simultaneously securing the stem 158 and plugging the opening 146. The fastener assembly 150 is inserted into a fastener head receiver 144 disposed in the upper front portion 114. The fastener head receiver 144 is coupled to an upper vertical slot 143 configured to accept the threaded stem 158, 159 of the fastener assembly 150 thereby allowing limited rotational motion of the stem 158. A dowel plug 145 may be used to fill any opening 146 left by the milling process. The fastener assembly 150 and upper body 111 mate to the lower body 130 with the threaded stem 158, 159 passing through a fastener opening 123 having the shape of a lower vertical slot 124, as shown in FIG. 5. The washer 160 and control 170 assemblies are disposed on the exposed, threaded end 159 of the stem 158 on the front side 133 of the lower body 130. The washer assembly 160 comprises a washer body 161 with a centrally disposed opening 162 configured to allow the stem 158 to pass through, and an interior portion 165 configured to mate with the control assembly 170. The control assembly 170 comprises a threaded knob 171 configured to receive a threaded end 159 of the stem 158. It is to be appreciated by those of skill in the art that any armature that provides for the tightening and loosening by the threads would be suitable to use in may offer additional advantages. The washer assembly 160 further comprises a spherical surface 166 configured to mate with a plurality of bowl-shaped recesses 125 disposed in the lower front portion 133 of the lower body 130 and along the lower vertical slot 124 and allow for smooth angular displacement of the fastener assembly 150 by the tightening of the control assembly 170. Alternatively, the surface of the washer may have a cylindrical shape with a plurality of matching cylindrical recesses disposed along the lower vertical slot 124 in the lower front portion 133 of the lower body 130.

Figure 7A:
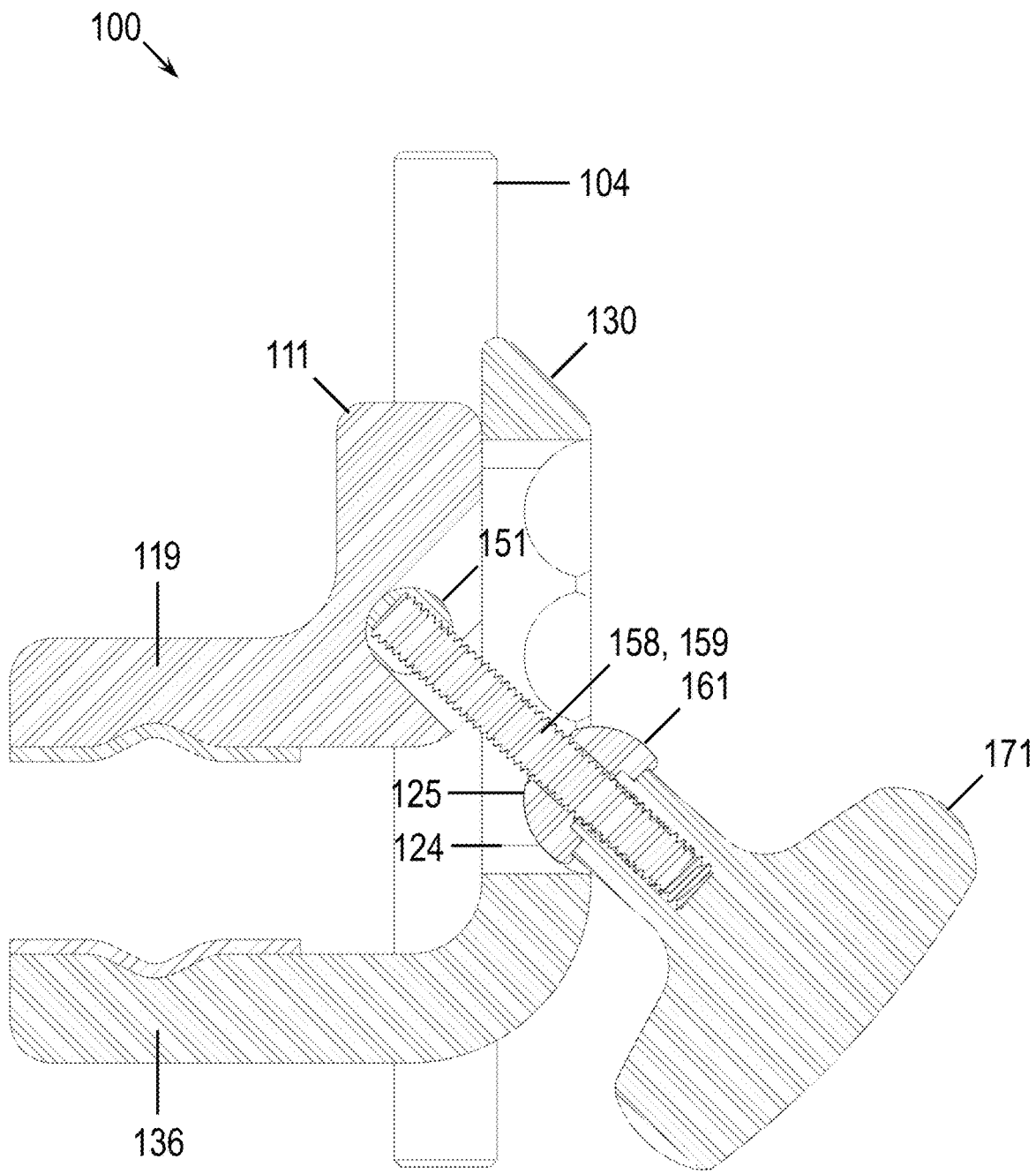
FIG. 7A illustrates a section view of the clamp apparatus of FIG. 5 in a first clamped position thereof.

The index clamping method 400 of the jogging clamp 100 may best be viewed in the sequence of operational steps outlined in FIGS. 7A-7E. In FIG. 7A, the jogging clamp 100 is shown in a first, clamped position wherein the control knob 171 is fully tightened on the stem 158, 159 forcing the washer 161 into a first bowl-shaped recesses 125. Tightening control assembly 170 forces the upper body 111 and the lower body 130, including upper 119 and lower 136 side rail arms, toward one another to achieve clamping forces in multiple directions, simultaneously: First, a clamping force may be achieved in a direction that allows upper and lower bodies 111 and 130 to fixedly attach to, for example, rail 102; second, a clamping force may be achieved in a direction that allows upper and lower bodies 111 and 130 to fixedly attach to, for example, a post 104. As previously described, the fastener head receiver 144, in conjunction with bowl-shaped recess 125 and spherical portion 166, provide for angular movement that achieves simultaneous clamping of multiple components, by allowing the T-segment 151 and stem 158 to rotate within the lower vertical slot 124.

Figure 7B:
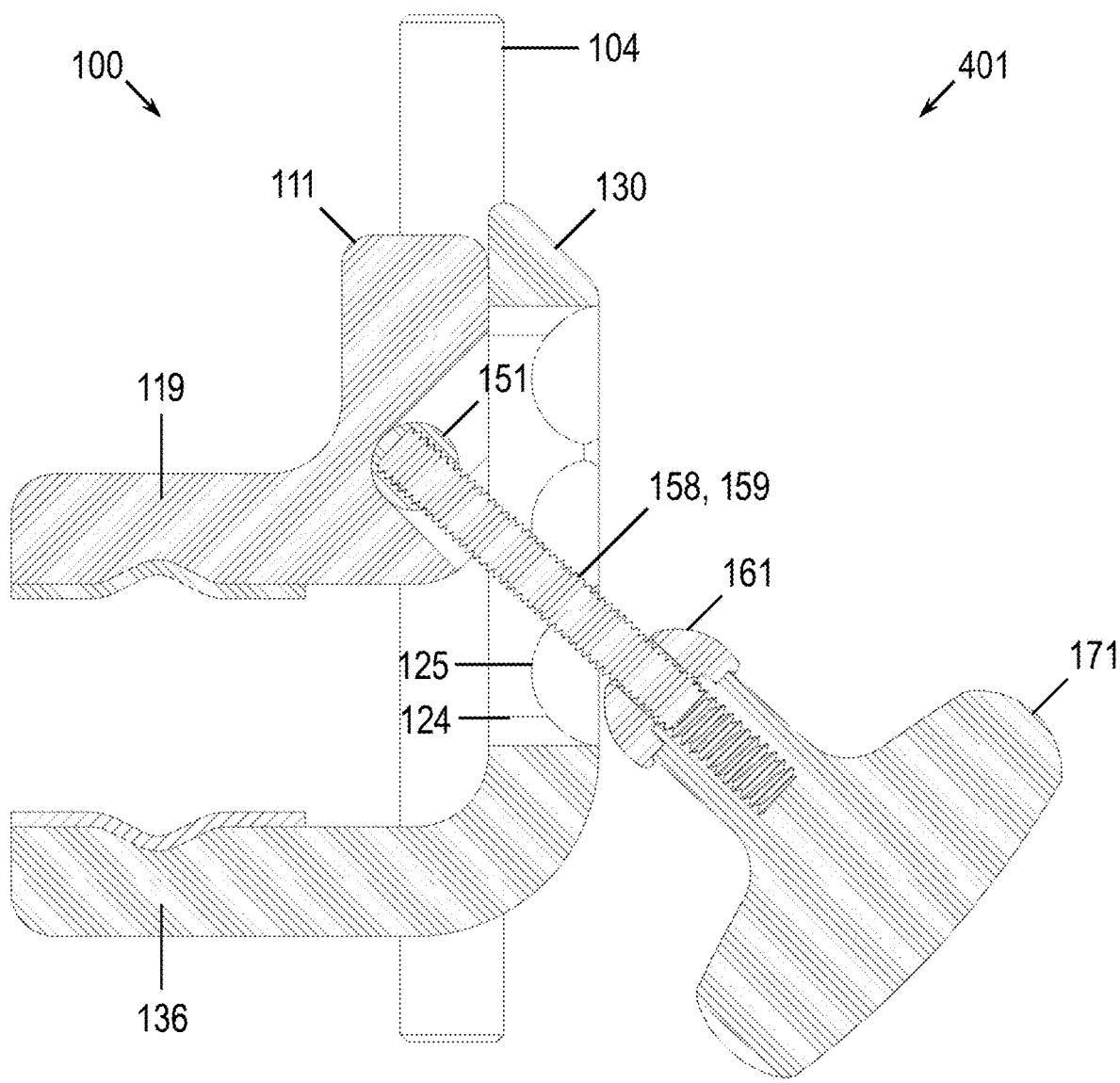
FIG. 7B illustrates a section view of the clamp apparatus of FIG. 5 in a first unclamped position thereof.

In a first index clamping step 401, shown in FIG. 7B, the jogging clamp 100 is moved to a first, unclamped position wherein the control knob 171 is loosely threaded on the stem 158, 159 allowing the washer 161 to disengage from the first bowl-shaped recess 125. A limited decoupling of the upper body 111 from the lower body 130 is possible in this configuration wherein the post 104 remains in the slot opening 118 of the upper body 111 and the through opening 117 of the lower body 130, allowing the post to slide freely.

Figure 7C:
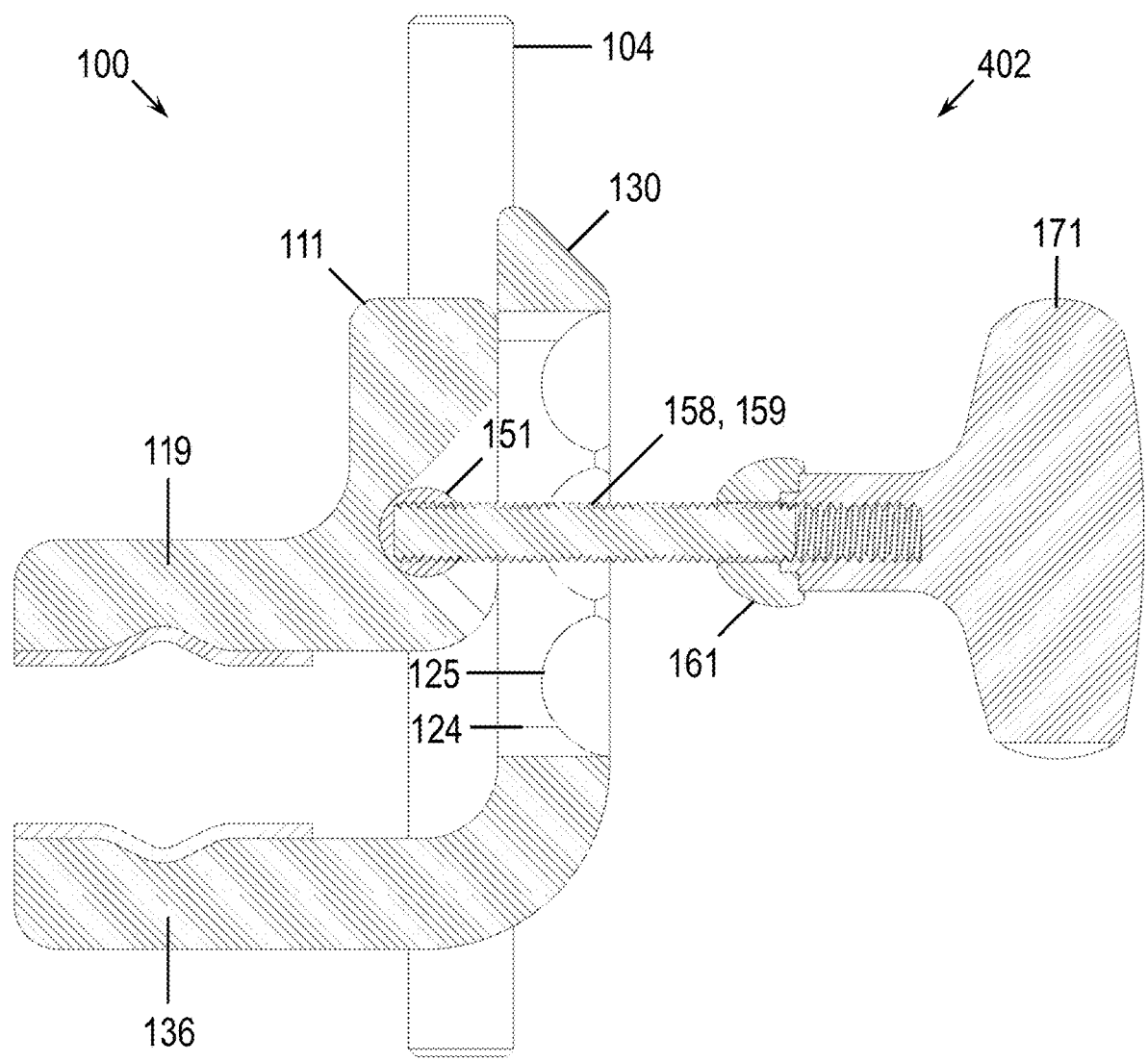
FIG. 7C illustrates a section view of the clamp apparatus of FIG. 5 in a jogging position thereof.

In a second index clamping step 402, shown in FIG. 7C, the jogging clamp 100 is shown in an open jogging position wherein the control knob 171 is loosely threaded on the stem 158, and both upper 111 and lower 130 bodies may freely slide relative to each other along the post 104. In this position, the upper body 111, fastener 150, washer, 160 and control 170 assemblies are translated together so as to accommodate a larger object to be inserted between upper 119 and lower 136 side rail arms.

Figure 7D:
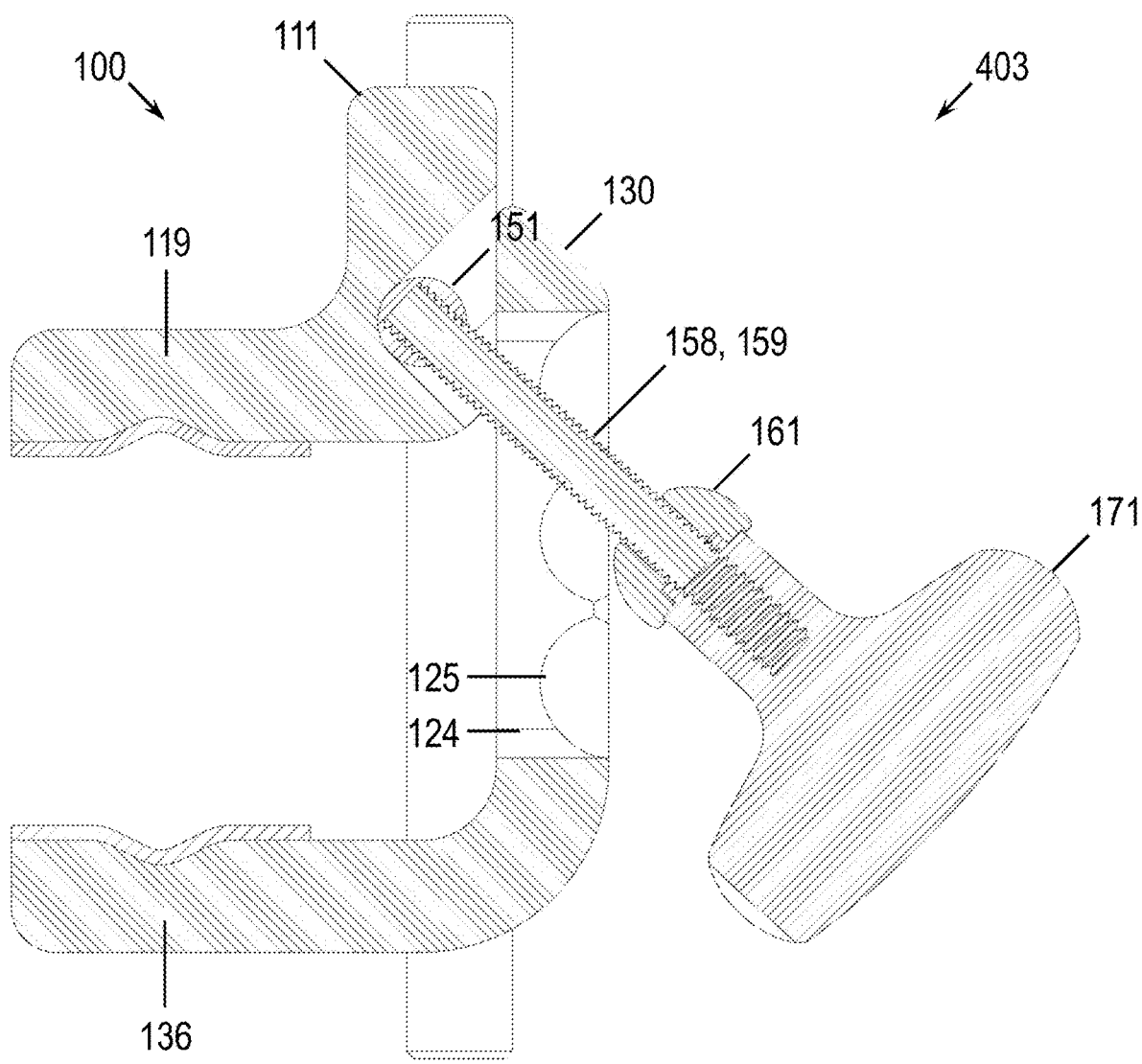
FIG. 7D illustrates a section view of the clamp apparatus of FIG. 5 in a second unclamped position thereof.

In a third index clamping step 403, shown in FIG. 7D, the jogging clamp 100 is moved to a second, unclamped position wherein the control knob 171 is loosely threaded on the stem 158, 159 allowing the washer 161 to align to and/or partially engage a second bowl-shaped recess 125.

Figure 7E:
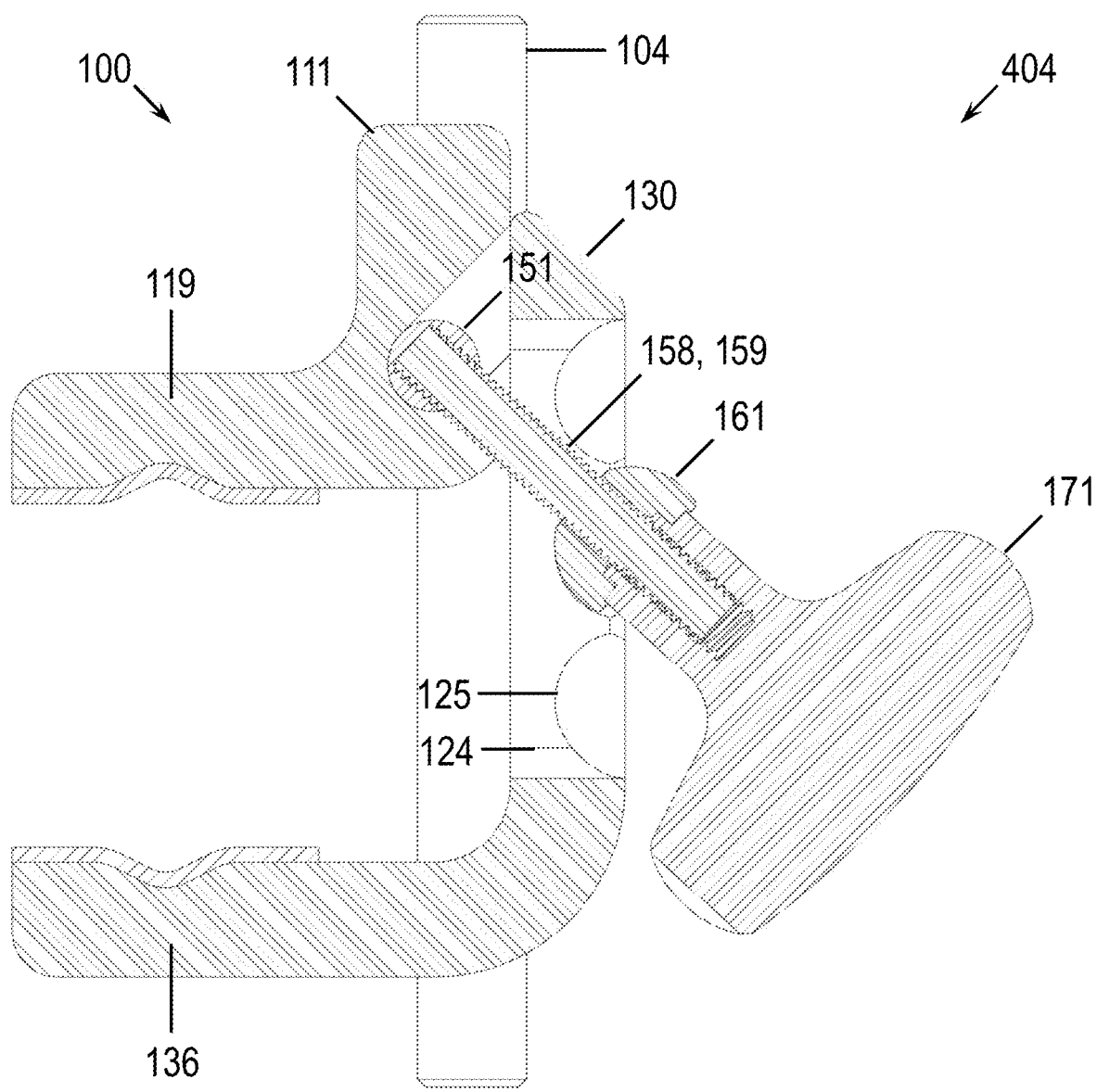
FIG. 7E illustrates a section view of the clamp apparatus of FIG. 5 in a second clamped position thereof.

In a fourth index clamping step 404, shown in FIG. 7E, the jogging clamp 100 is closed around a rail, tube or other object (not shown). The control knob 171 is tightened on the stem 158, 159 forcing the washer 161 into the second bowl-shaped recesses 125 thereby urging the upper 111 and lower 130 bodies, including upper 119 and lower 136 side rail arms, toward one another to achieve clamping on the rail and post 104 simultaneously.

The index clamping method 400 may be varied by selecting alternate indexing positions, as defined by the bowl-shaped recesses 125 to accommodate larger or smaller primary clamping surfaces. The size of the simultaneously clamped post 104, however, is defined by the diameter of the slot recess 117 and opening 118 and must be predetermined based on the application. The concepts disclosed herein with respect to the various embodiments are combinable, interchangeable, and non-limiting in that respect. For example, one skilled in the art will recognize that the jogging clamp 100 may be combined with certain embodiments described herein, as the intended purpose may serve.

While certain configurations of structures have been illustrated for the purposes of presenting the basic structures of the present invention, one of ordinary skill in the art will appreciate that other variations are possible which would still fall within the scope of the appended claims. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A clamp comprising:
   an upper body including:
      an upper base;
      an upper arm extending outwardly from said upper base;
      a channel portion formed in said upper base bottom portion configured to receive a key protrusion; and
      one or more slot-shaped fastener openings extending through said upper base;
   a lower body including:
      a lower base,
      a lower arm extending outwardly from said lower base, said upper and lower arms being adapted to clamp or couple to one or more first objects,
      one or more fastener head openings formed through said lower base, each of said fastener head openings having at least one rotational inhibitor;
      a key protrusion extending outwardly from said lower base, said key protrusion forming a complementary shape with said channel portion when said upper and lower bodies are in an assembled configuration, and
      a lower bottom portion, said lower bottom portion and said one or more openings being adapted to clamp or couple to one or more second objects;
   a fastener assembly comprising a bolt head and a threaded portion, said fastener assembly configured to be received and extend through each of said one or more fastener openings and said one or more fastener head openings, said bolt head having at least one protrusion, said bolt head being configured to be received by said fastener head opening, said at least one rotational inhibitor and said at least one protrusion being adapted to prohibit rotation of the fastener assembly with respect to said upper and/or lower bodies, said fastener assembly further configured to translate along said one or more slot-shaped fastener openings to provide slidable adjustment of said threaded portion through said fastener opening; and
   a control assembly operably connected to said fastener assembly, said control assembly configured to advance along said threaded portion of said fastener assembly to urge said upper and lower body portions together to achieve simultaneous, multi-directional clamping of said one or more first and said one or more second objects.

2. The clamp according to claim 1, further comprising a washer assembly including a body and a washer opening extending therethrough and configured to receive said threaded portion of said fastener assembly.

3. The clamp according to claim 1, wherein said bolt head comprises six protrusions formed as a hex bolt, said one or more fastener head openings comprising a corresponding six notches.

4. A clamp comprising:
   an upper body including:
      an upper base;
      an upper arm extending outwardly from said upper base;
      a fastener head receiver formed in said upper base;
      an upper transverse opening formed along a portion of said upper base in said upper body intersecting said fastener head receiver; and
      an upper vertical slot formed in said upper front portion, said upper vertical slot intersecting said fastener head receiver;
   a lower body including:
      a lower base;
      a lower arm extending outwardly from said lower base, said upper and lower arms being adapted to clamp or couple to one or more first objects,
      a plurality of spherical recesses formed along said lower base in a lower front portion; and
      a lower vertical slot formed in said lower front portion intersecting said plurality of spherical recesses;
   a fastener assembly comprising a T-portion and a threaded portion, said threaded portion configured to be received and extend through said upper and lower transverse openings, said T-portion configured to be received and translationally fixed within said fastener head receiver, said fastener assembly further configured to rotate about said T-portion to provide angular adjustment of said threaded portion through said upper and lower vertical slots; and
   a control assembly operably coupled to said threaded portion of said fastener assembly, said control assembly configured to advance along said threaded portion to urge a portion of said control assembly into a spherical recess of said plurality of spherical recesses, thereby urging said upper and lower bodies together to achieve simultaneous, multi-directional clamping of said first and second objects.

5. The clamp according to claim 4, wherein said portion of said control assembly comprises a washer forming a complementary shape as that of one spherical recess of said plurality of spherical recesses.

6. A method of adjusting a clamp for clamping to variable-sized first objects, the method comprising:
   providing the clamp according to claim 4;
   loosening said control assembly so as to disengage said control assembly from a first spherical recess of said plurality of spherical recesses;
   rotating the control assembly about said T-portion so that said an upper body is slidably moveable relative to said lower body;
   aligning said control assembly with a second spherical recess of said plurality of spherical recesses; and
   tightening said control assembly so as to engage said control assembly with said second spherical recess, thereby moving said upper and lower bodies, thereby effecting a clamping action.

7. The method according to claim 6, wherein said portion of said control assembly comprises a washer forming a complementary shape as that of one spherical recess of said plurality of spherical recesses.

\* \* \* \* \*